United States Patent
Fujii et al.

(10) Patent No.: US 6,570,025 B1
(45) Date of Patent: May 27, 2003

(54) SULFUR COMPOUND AND USE THEREOF

(75) Inventors: Kenichi Fujii, Kanagawa (JP); Atsuo Otsuji, Chiba (JP); Masao Imai, Kanagawa (JP); Kenichi Sugimoto, Kanagawa (JP); Tadashi Okuma, Chiba (JP); Rihoko Suzuki, Chiba (JP); Keisuke Takuma, Kanagawa (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/048,002

(22) PCT Filed: Aug. 10, 2000

(86) PCT No.: PCT/JP00/05368

§ 371 (c)(1),
(2), (4) Date: Jan. 25, 2002

(87) PCT Pub. No.: WO01/92252

PCT Pub. Date: Dec. 6, 2001

(30) Foreign Application Priority Data

May 31, 2000 (JP) ........................................ 2000-162899

(51) Int. Cl.[7] ................... C07D 339/06; C07D 339/08; C07D 339/00
(52) U.S. Cl. .............................. 549/11; 549/22; 549/39
(58) Field of Search ................................ 549/39, 11, 22

(56) References Cited

FOREIGN PATENT DOCUMENTS

| EP | WO 98/35955 | 8/1998 |
|---|---|---|
| JP | 4-321662 | 11/1992 |
| JP | 4-323209 | 11/1992 |
| WO | 0 550 998 A1 | 7/1993 |

*Primary Examiner*—Alan L. Rotman
*Assistant Examiner*—Rebecca Anderson
(74) *Attorney, Agent, or Firm*—Burns, Doane, Swecker & Mathis, LLP

(57) ABSTRACT

This invention provides sulfur-containing (meth)acrylic ester compounds each of which is represented by the following formula (1);

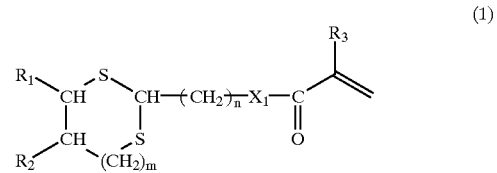

(1)

wherein $R_1$ and $R_2$ each independently represent a hydrogen atom or an alkyl group or may be fused together to form a ring, $R_3$ represents a hydrogen atom or a methyl group, $X_1$ represents an oxygen atom or a sulfur atom, m stands for an integer of from 0 to 3, and n stands for an integer of from 1 to 4, polymerizable compositions comprising the sulfur-containing (meth)acrylic acids, and cured products and optical parts obtained by polymerizing the polymerizable compositions. The sulfur-containing (meth)acrylic ester compounds according to the present invention are very useful, as monomers for photocurable, polymerizable compositions, in applications such as optical materials and dental materials. The optical parts obtained by curing the polymerizable compositions are excellent in optical properties, thermal properties and mechanical properties and are also good in productivity.

1 Claim, No Drawings

SULFUR COMPOUND AND USE THEREOF

This application is a 371 of PCT/JP00/05368 with international filing date of Aug. 10, 2000.

TECHNICAL FIELD

This invention relates to a sulfur-containing (meth)acrylic ester compound. The present invention is also concerned with a polymerizable composition comprising the sulfur-containing (meth)acrylic ester compound, and also with an optical part obtained by polymerizing the polymerizable composition.

The sulfur-containing (meth)acrylic ester compound according to the present invention has a characteristic feature in molecular structure that contains a cyclic thioacetal structure in its molecule, and is useful as a monomer for a photocurable, polymerizable composition. The optical part obtained by curing the polymerizable composition is excellent in optical properties, thermal properties and mechanical properties, is good in productivity and has high refractive index, so that it is useful as various plastic lenses represented by correctional eyeglass lenses, substrates for optical information recording media, plastic substrates for liquid crystal cells, coating materials for optical fibers, and the like.

BACKGROUND ART

Inorganic glass is excellent in various physical properties as typified by excellent transparency and small optical anisotropy, and therefore, is used as a transparent optical material in a wide variety of fields. Nonetheless, it involves problems such as heavy weight, fragility and poor productivity, and in recent years, developments of optical resins as replacements for inorganic glass are actively under way.

As an optical resin, a fundamentally important property is transparency. Industrial optical resins known to date to have good transparency include polymethyl methacrylate (PMMA), bisphenol A polycarbonate (BPA-PC), polystyrene (PS), methyl methacrylate-styrene copolymer (MS), styrene-acrylonitrile copolymer (SAN), poly(4-methylpentene-1) (TPX), polycycloolefins (COPs), polydiethylene glycol bis(allyl carbonate) (EGAC), polythiourethanes (PTUs), and the like.

PMMA is excellent in transparency and weatherability and is also good in moldability. It, however, involves drawbacks in that it has a refractive index (nd) as low as 1.49 and high water absorption property.

BPA-PC has a large chromatic aberration so that a limitation is imposed on its application fields, although it is excellent in transparency, heat resistance, impact resistance and high refraction properties.

PS and MS are excellent in moldability, transparency, low water absorption property, and high refraction properties. They are, however, inferior in impact resistance, weatherability and heat resistance so that they have not found any substantial practical utility as optical resins.

SAN is relatively high in refractive index and its mechanical properties are considered to be well-balanced. However, SAN is somewhat defective in heat resistance (heat distortion temperature: 80 to 90° C.) and practically, is not used as an optical resin.

TPX and COPs are excellent in transparency and heat resistance, and have low water absorption property. They are, however, accompanied by problems in that they are low in refractive index (nd: 1.47 to 1.53) and are poor in impact resistance, gas barrier property and dyeability.

EGAC is a thermosetting resin available from diethylene glycol bis(allyl carbonate) as a monomer, and is used most widely for general-purpose eyeglass lenses. Although it is excellent in transparency and heat resistance and is extremely small in chromic aberration, it has drawbacks in that it is low in refractive index (nd=1.50) and is inferior in impact resistance.

PTUs are thermosetting resins each of which are obtained by a reaction between a diisocyanate compound and a polythiol compound, and are used most widely for eyeglass lenses of high refractive index. They are extremely good materials for their outstanding transparency, impact resistance, high refractive properties and their small chromic aberration. They are, however, deficient only in that they require long thermopolymerization molding time (1 to 3 days), and are still accompanied by an unsolved problem in productivity.

With a view to achieving polymerization and curing in a short time to increase their productivity, certain production processes have been proposed, including photopolymerization of a bromine- or sulfur-containing acrylic ester to obtain an optical lens (e.g., JP 4-161410 A, JP 3-217412 A) and use of a (meth)acrylic ester compound having a sulfur-containing alicyclic structure for the production of an optical lens (e.g., JP 3-215801 A).

These processes make it possible to achieve polymerization in a short time, but the resulting resins are by no means satisfactory for optical parts. Described specifically, when these resins are used as eyeglass lenses, for example, those having high refractive indexes involve problems in that they are brittle and susceptible to breakage and are high in specific gravity. There is, accordingly, a strong desire for the development of a material free of these problems.

As has been described above, it is the current circumstance that each of the conventional optical resins still has one or more drawbacks to be solved although it has certain excellent properties. Under the foregoing situation, it is the current circumstance that a keen desire exists for the development of an optical resin excellent in optical properties, mechanical properties and thermal properties and high in productivity and refractive index.

DISCLOSURE OF THE INVENTION

An object of the present invention is, therefore, to solve the above-described drawbacks of the conventional optical resins, and to provide a monomer as a raw material for an optical material excellent in optical properties, mechanical properties and thermal properties and high in productivity and refractive index and also to provide an intermediate for the monomer.

The present inventors have proceeded with an extensive investigation to achieve the above-described object and as a result, have reached the present invention. Specifically, the present invention relates to a sulfur-containing (meth)acrylic ester compound represented by the following formula (1):

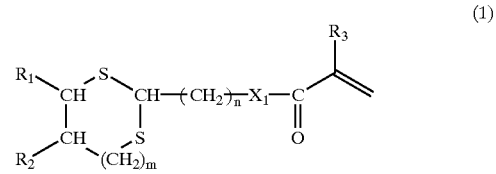

wherein $R_1$ and $R_2$ each independently represent a hydrogen atom or an alkyl group or may be fused together to form a ring, $R_3$ represents a hydrogen atom or a methyl group, $X_1$ represents an oxygen atom or a sulfur atom, m stands for an integer of from 0 to 3, and n stands for an integer of from 1 to 4.

The present invention also relates to a polymerizable composition comprising the sulfur-containing (meth)acrylic ester compound represented by formula (1), a cured product obtained by polymerizing the polymerizable composition, and further, an optical part comprising the cured product.

BEST MODES FOR CARRYING OUT THE INVENTION

The present invention will hereinafter be described in detail.

The sulfur-containing (meth)acrylic ester compound according to the present invention, which is represented by formula (1), is a novel compound, and is a (meth)acrylic ester characterized by the possession of a cyclic thioacetal structure in the moiety of the ester group.

In formula (1), $R_1$ and $R_2$ each independently represent a hydrogen atom or an alkyl group. As an alternative, $R_1$ and $R_2$ may be fused together to form a ring.

Each of the substituents $R_1$ and $R_2$ may preferably be a hydrogen atom or an alkyl group having 1 to 4 carbon atoms, with a hydrogen atom, a methyl group or an ethyl group being more preferred. When $R_1$ and $R_2$ are fused together to form a ring, the ring may be preferably a cycloalkane ring, more preferably a cycloalkane ring having 5 to 7 carbon atoms, still more preferably a cyclohexane ring.

In formula (1), m is an integer of from 0 to 3, preferably an integer of from 0 to 2, more preferably an integer of 0 or 1.

In formula (1), n is an integer of from 1 to 4, preferably an integer of from 1 to 3, more preferably an integer of 1 or 2.

In formula (1), $X_1$ represents an oxygen atom or a sulfur atom. In view of a high refractive index required upon using as a lens resin, $X_1$ is preferably a sulfur atom.

As specific examples of the sulfur-containing (meth) acrylic ester compound represented by formula (1) according to the present invention, the compounds shown below in Table 1 can be exemplified.

TABLE 1

| Illustrative Compound No. | Structural formula |
|---|---|
| 1-1 | |
| 1-2 | |
| 1-3 | |
| 1-4 | |
| 1-5 | |
| 1-6 | |
| 1-7 | |
| 1-8 | |
| 1-9 | |
| 1-10 | |
| 1-11 | |
| 1-12 | |
| 1-13 | |
| 1-14 | |
| 1-15 | |

TABLE 1-continued

| Illustrative Compound No. | Structural formula |
|---|---|
| 1-16 | (1,3-dithiolan-2-yl)-(CH₂)₂-O-C(=O)-CH=CH₂ |
| 1-17 | (1,3-dithiolan-2-yl)-(CH₂)₃-O-C(=O)-CH=CH₂ |
| 1-18 | (1,3-dithiolan-2-yl)-(CH₂)₄-O-C(=O)-CH=CH₂ |
| 1-19 | (4-methyl-1,3-dithiolan-2-yl)-(CH₂)₂-O-C(=O)-CH=CH₂ |
| 1-20 | (4-ethyl-1,3-dithiolan-2-yl)-(CH₂)₂-O-C(=O)-CH=CH₂ |
| 1-21 | (4-n-butyl-1,3-dithiolan-2-yl)-(CH₂)₂-O-C(=O)-CH=CH₂ |
| 1-22 | (4,5-dimethyl-1,3-dithiolan-2-yl)-(CH₂)₂-O-C(=O)-CH=CH₂ |
| 1-23 | (hexahydro-1,3-benzodithiol-2-yl)-(CH₂)₂-O-C(=O)-CH=CH₂ |
| 1-24 | (1,3-dithian-2-yl)-CH₂-O-C(=O)-CH=CH₂ |
| 1-25 | (1,3-dithian-2-yl)-(CH₂)₂-O-C(=O)-CH=CH₂ |
| 1-26 | (1,3-dithian-2-yl)-(CH₂)₃-O-C(=O)-CH=CH₂ |
| 1-27 | (1,3-dithian-2-yl)-(CH₂)₄-O-C(=O)-CH=CH₂ |
| 1-28 | (1,3-dithiepan-2-yl)-(CH₂)₂-O-C(=O)-CH=CH₂ |
| 1-29 | (1,3-dithiolan-2-yl)-CH₂-S-C(=O)-C(CH₃)=CH₂ |
| 1-30 | (1,3-dithiolan-2-yl)-(CH₂)₂-S-C(=O)-C(CH₃)=CH₂ |
| 1-31 | (1,3-dithiolan-2-yl)-(CH₂)₃-S-C(=O)-C(CH₃)=CH₂ |
| 1-32 | (1,3-dithiolan-2-yl)-(CH₂)₄-S-C(=O)-C(CH₃)=CH₂ |
| 1-33 | (4-methyl-1,3-dithiolan-2-yl)-(CH₂)₂-S-C(=O)-C(CH₃)=CH₂ |
| 1-34 | (4-ethyl-1,3-dithiolan-2-yl)-(CH₂)₂-S-C(=O)-C(CH₃)=CH₂ |
| 1-35 | (4-n-butyl-1,3-dithiolan-2-yl)-(CH₂)₂-S-C(=O)-C(CH₃)=CH₂ |
| 1-36 | (4,5-dimethyl-1,3-dithiolan-2-yl)-(CH₂)₂-S-C(=O)-C(CH₃)=CH₂ |
| 1-37 | (hexahydro-1,3-benzodithiol-2-yl)-(CH₂)₂-S-C(=O)-C(CH₃)=CH₂ |
| 1-38 | (1,3-dithian-2-yl)-CH₂-S-C(=O)-C(CH₃)=CH₂ |
| 1-39 | (1,3-dithian-2-yl)-(CH₂)₂-S-C(=O)-C(CH₃)=CH₂ |
| 1-40 | (1,3-dithian-2-yl)-(CH₂)₃-S-C(=O)-C(CH₃)=CH₂ |

TABLE 1-continued

| Illustrative Compound No. | Structural formula |
|---|---|
| 1-41 | |
| 1-42 | |
| 1-43 | |
| 1-44 | |
| 1-45 | |
| 1-46 | |
| 1-47 | |
| 1-48 | |
| 1-49 | |
| 1-50 | |
| 1-51 | |
| 1-52 | |
| 1-53 | |

TABLE 1-continued

| Illustrative Compound No. | Structural formula |
|---|---|
| 1-54 | |
| 1-55 | |
| 1-56 | |

These sulfur-containing (meth)acrylic ester compounds represented by formula (1) according to the present invention can each be produced by conducting, on a compound represented by the following formula (2-a) or the following formula (2-b), desired one of various known esterification processes (or thioesterification processes) typified specifically by:

(1) a process in which a (meth)acrylic acid or the like is reacted; and (2) a process in which a halopropionic ester compound (for example, 3-chloropropionic acid, 3-bromopropionic acid, 3-chloro-2-methylpropionic acid, 3-bromo-2-methylpropionic acid, or the like) or an acid halide thereof is reacted to form a halopropionic ester derivative, followed by the dehydrohalogenation of the derivative into the (meth)acrylic ester.

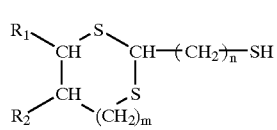

(2-a)

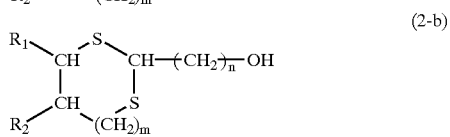

(2-b)

wherein $R_1$, $R_2$, m and n have the same meanings as defined above.

Among the processes described above, the latter process (2) is more preferred as a process for producing each sulfur-containing (meth)acrylic ester compound represented by formula (1) according to the present invention.

As a most representative example of the above-mentioned processes, a more detailed description will hereinafter be made firstly about a process in which a sulfur-containing compound represented by formula (2-a) or formula (2-b) and a (meth)acrylic acid or the like [(meth)acrylic acid, an ester derivative, or an acid halide thereof] are reacted.

Specifically, a known process, for example, a process similar to that disclosed in J. Org. Chem., 45, 5364 (1980) or Eur. Polym. J., 19, 399 (1983) can be used as the above process.

Illustrative is:
(1) a process in which an acid halide of (meth)acrylic acid is caused to act on a sulfur-containing compound represented by formula (2-a) or formula (2-b) under stirring in the presence of a base by a procedure such as dropwise addition of the acid halide;
(2) a process in which a sulfur-containing hydroxy compound represented by formula (2-b) and (meth)acrylic acid are subjected to a dehydrating reaction in the presence of a catalyst; or
(3) a process in which a sulfur-containing hydroxy compound represented by formula (2-b) and a (meth)acrylic ester derivative [for example, an alkyl (meth)acrylate such as methyl (meth)acrylate, ethyl (meth)acrylate or butyl (meth)acrylate] are subjected to an ester interchange reaction in the presence of a catalyst (acid catalyst or base catalyst).

No particular limitation is imposed on the amount of the (meth)acrylic acid or the like [(meth)acrylic acid, an ester derivative thereof, or an acid halide thereof] which is caused to act on the sulfur-containing compound represented by formula (2-a) or formula (2-b) in the above-described reaction. In general, however, the (meth)acrylic acid or the like may be used in a proportion of from 0.1 to 5 moles, with 0.25 to 2.5 moles being preferred and 0.4 to 1.5 moles being more preferred, all per mole of the sulfur-containing compound.

The reaction can be conducted in a solventless manner, or can be conducted in a solvent which is inert to the reaction. Examples of such a solvent can include hydrocarbon solvents such as n-hexane, benzene and toluene; ketone solvents such as acetone, methyl ethyl ketone and methyl isobutyl ketone; ester solvents such as ethyl acetate and butyl acetate; ether solvents such as diethyl ether, tetrahydrofuran and dioxane; halogenated solvents such as dichloromethane, chloroform, carbon tetrachloride, 1,2-dichloroethane and Perclene; and polar solvents such as acetonitrile, N,N-dimethylformamide, N,N-dimethylacetamide and N,N-dimethylimidazolidinone. Two or more of these solvents may be used without development of inconvenience.

No particular limitation is imposed on the reaction temperature. The reaction should, however, be conducted at such a temperature that neither the (meth)acrylic acid or the like as a raw material nor the sulfur-containing (meth)acrylic ester compound as a reaction product is allowed to undergo polymerization. In general, the reaction temperature may be in a range of from −78 to 150° C., with −20 to 120° C. being preferred and 0 to 100° C. being more preferred.

The reaction time is also dependent upon the reaction temperature. In general, however, the reaction time may range from several minutes to 100 hours, with 30 minutes to 50 hours being preferred and 1 to 20 hours being more preferred. As an alternative, the reaction can be terminated at a desired rate of reaction while monitoring the rate of reaction by a known analyzing means (for example, liquid chromatography, thin layer chromatography, IR or the like).

Upon producing the sulfur-containing (meth)acrylic ester compound according to the present invention by the reaction between sulfur-containing compound represented by formula (2-a) or formula (2-b) and the acid halide of (meth)acrylic acid, hydrogen halide (for example, hydrogen chloride or the like) is byproduced. For example, an organic base such as triethylamine, pyridine, picoline, dimethylaniline, diethylaniline, 1,4-diazabicyclo[2.2.2] octane (DABCO) or 1,8-diazabicyclo[5.4.0]undeca-7-ene (DBU) or an inorganic base such as sodium hydrogencarbonate, sodium carbonate, potassium carbonate, lithium carbonate, sodium hydroxide, potassium hydroxide, calcium hydroxide or magnesium oxide may, therefore, be used as a dehydrohalogenating agent.

Although no particular limitation is imposed on the amount of such a dehydrohalogenating agent to be used, it may be used in a proportion of from 0.05 to 10 moles, preferably from 0.1 to 5 moles, more preferably from 0.5 to 3 moles per mole of the sulfur-containing compound represented by formula (2).

Upon producing the sulfur-containing (meth)acrylic ester compound represented by formula (1) according to the present invention by the dehydrating reaction between the sulfur-containing hydroxy compound represented by formula (2-b) and (meth)acrylic acid, use of desired one of various known esterification catalysts is preferred. Illustrative of the catalysts are mineral acids (for example, hydrochloric acid, sulfuric acid, nitric acid, boric acid, phosphoric acid, and the like); organic acids (for example, methanesulfonic acid, benzenesulfonic acid, p-toluenesulfonic acid, trifluoromethanesulfonic acid, and the like); and Lewis acids (for example, boron trifluoride, aluminum trichloride, titanium tetrachloride, titanium dichloride, tin dichloride, tin tetrachloride, and the like).

No particular limitation is imposed on the amount of such a catalyst to be used. In general, however, it may be used preferably in a proportion of from 0.001 to 50 wt. %, more preferably in a proportion of from 0.01 to 30 wt. % based on the reaction feed mixture.

For the acceleration of the progress of the reaction, it is preferred to remove byproduced water from the system. Examples of a method for effecting this removal include azeotropic dehydration by use of one of the above-exemplified solvents, said one solvent being capable of forming an azeotropic mixture (for example, a hydrocarbon solvent such as benzene, toluene or xylene); use of a dehydrating agent such as molecular sieve; and combined use of these methods.

Among the above-mentioned processes, the process—in which the sulfur-containing (meth)acrylic ester compound represented by formula (1) is produced by reacting the halopropionic ester compound represented by formula (2-a) or formula (2-b) with the halopropionic acid or its acid halide to form a halopropionic ester compound and then dehydrohalogenating the halopropionic ester compound—can be typified, for example, by the process disclosed in JP 10-67736 A or the like.

Upon producing the sulfur-containing (meth)acrylic ester compound represented by formula (1) according to the present invention, use of a polymerization inhibitor for the prevention of polymerization of the reaction product during the reaction or after the reaction is preferred. As examples of such a polymerization inhibitor, a variety of known compounds such as 4-methoxyphenol, hydroquinone and phenothiazine can be mentioned. No particular limitation is imposed on the amount of the polymerization inhibitor to be used. In general, however, the polymerization inhibitor may be used in a proportion of from 0.01 to 5 wt. %, preferably from 0.05 to 3 wt. % based on the reaction feed mixture or the reaction product in the reaction system.

After completion of the reaction, the reaction product, i.e., the sulfur-containing (meth)acrylic ester compound represented by formula (1) according to the present invention is post-treated and isolated by known procedure and treatment methods (typically, neutralization, extraction into solvent, washing with water, separation into layers, removal of solvent by distillation, etc.). If necessary, the thus-obtained sulfur-containing (meth)acrylic ester compound represented by formula (1) may be separated and purified by a known method (for example, distillation, recrystallization, chromatography or the like) to isolate as a high-purity compound.

The compound represented by formula (2-a) or (2-b), namely, the hydroxyl-containing compound (2-b) or the thiol-containing compound (2-a) can be appropriately produced by converting the halogen atom in a cyclic thioacetal compound, which is represented by the below-described formula (2-c), in accordance with a known synthetic chemical procedure, for example, by subjecting the halogen atom to alkaline hydrolysis to convert the same into a hydroxyl group or by causing thiourea to act on the halogen atom to form a thiouronium salt and then subjecting it to alkaline treatment to form a thiol group.

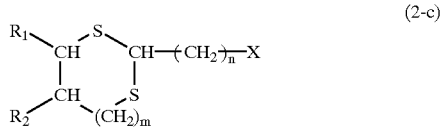

wherein $R_1$, $R_2$, m and n have the same meanings as defined above, and X represents a halogen atom.

Further, the conversion from the halogen derivative represented by formula (2-c) into the thiol group can be appropriately practiced by a known process, for example, by the process disclosed in Journal of Organic Chemistry, 27, 93–95 (1962) or Organic Synthesis, IV, 401–403 (1963). Described specifically, according to such a representative process, the compound of formula (2-a) can be appropriately produced by reacting thiourea to X (i.e., halogen atom) in formula (2-c) and then hydrolyzing the thus-formed group with a base such as aqueous ammonia or sodium hydroxide.

The sulfur-containing compound represented by formula (2-c), which is useful as a raw material in the present invention, can be appropriately produced typically by reacting a dithiol represented by the following formula (4) with an aldehyde represented by the following formula (3) or a derivative thereof in the presence of an acid catalyst.

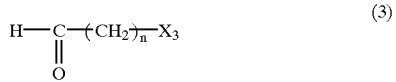

wherein $X_3$ represents a halogen atom, and n stands for an integer of from 1 to 4.

wherein $R_1$, $R_2$ and m have the same meanings as defined above.

A more detailed description will hereinafter be made firstly about the process in which the compound represented by formula (2-c) is produced by reacting the dithiol represented by formula (4) to the aldehyde represented by formula (3) or the like in the presence of the acid catalyst.

Illustrative of the aldehyde represented by formula (3) or its derivative are: haloalkyl aldehydes such as chloroacetaldehyde, 3-chloropropionaldehyde, 3-bromopropionaldehyde, 4-chlorobutyraldehyde, and 4-bromobutyraldehyde; and dialkyl acetal derivatives or cyclic alkylene acetal derivatives or the like of haloalkyl aldehydes, such as 2-chloroacetaldehyde dimethyl acetal, 2-chloroacetaldehyde diethyl acetal, 2-chloropropionaldehyde dimethyl acetal, 2-chloropropionaldehyde diethyl acetal, 2-bromopropionaldehyde diethyl acetal, 2-bromopropionaldehyde ethylene acetal [or 2-(2'-bromoethyl)-1,3-dioxolane], and 2-bromopropionaldehyde trimethylene acetal [or 2-(2'-bromo-ethyl)-1,3-dioxane].

Illustrative of the dithiol derivative represented by formula (4) are:

linear alkanedithiols such as ethanedithiol, 1,2-propanedithiol, 1,3-propanedithiol, 1,2-butanedithiol, 1,3-butanedithiol, 1,4-butanedithiol, 1,2-pentanedithiol, 1,3-pentanedithiol, 1,4-pentanedithiol, 1,2-hexanedithiol, 1,3-hexanedithiol, 1,4-hexanedithol, 1,2-heptanedithol, 1,2-octanedithiol, 1,2-nonanedithiol, and 1,2-decanedithiol; and cycloalkanedithiols such as cyclopentane-1,2-dithiol and cyclohexane-1,2-dithiol.

No particular limitation is imposed on the amount of the dithiol represented by formula (4) which is to be used upon producing the compound of formula (2-c) by reacting the dithiol represented by formula (4) with the aldehyde represented by formula (3) or its derivative. In general, however, the dithiol represented by formula (4) may be used in a proportion of from 0.5 to 5 moles per mole of the aldehyde represented by formula (3) or its derivative, with 0.8 to 2 moles being preferred and 0.9 to 1.2 moles being more preferred.

In such a reaction, the reaction may be conducted under solventless conditions or in the presence of a catalyst such as a protonic acid, for example, a mineral acid (e.g., hydrochloric acid or sulfuric acid) or an organic acid (e.g., acetic acid or propionic acid), or a Lewis acid. In view of the reaction temperature, reaction time and the like, it is preferred to conduct the reaction in the presence of the catalyst for the purpose of accelerating the reaction.

Illustrative of such reaction catalysts are:

protonic acids such as sulfuric acid, hydrochloric acid, hydrobromic acid, nitric acid, acetic acid, propionic acid, methanesulfonic acid, trifluoromethanesulfonic acid, and p-toluenesulfonic acid; and Lewis acids such as titanium trichloride, titanium tetrachloride, tin dichloride, tin tetrachloride, boron trifluoride-ether complexes.

No particular limitation is imposed on the amount of such a reaction catalyst to be used. In general, however, the reaction catalyst may be used in a proportion of from 0.001 mole to 20 moles per mole of the aldehyde represented by formula (3) or its derivative, with 0.01 mole to 10 moles being preferred and 0.1 mole to 5 moles being more preferred. These reaction catalysts may be used either singly or in combination.

The reaction can be conducted either in a solventless manner or in the presence of a solvent. When a solvent is used, no particular limitation is imposed on the solvent insofar as it is inert to the reaction. Examples of the solvent include hydrocarbon solvents such as benzene, toluene and xylene; halogenated solvents such as methylene chloride, chloroform, 1,2-dichloroethane, chlorobenzene and dichlorobenzene; and ether-type solvents such as diethyl ether, tetrahydrofuran, dioxane and diethylene glycol dimethyl ether. These solvents may be used either singly or in combination.

No particular limitation is imposed on the amount of the reaction solvent to be used. From the standpoint of production efficiency and the like, however, it is not preferred to use the reaction solvent in an excessively large amount. The reaction solvent may, therefore, be used generally in a weight proportion not greater than 300 times, preferably in a weight proportion not greater than 100 times the aldehyde represented by formula (3) or its acetal derivative.

The reaction may be conducted either under the surrounding atmosphere or under an inert gas atmosphere. To control coloration or the like of the reaction production, however, it is preferred to conduct the reaction under an inert gas atmosphere such as nitrogen or argon.

No particular limitation is imposed on the reaction temperature. In general, however, it is preferred to conduct the reaction in a range of from 0° C. to the boiling point of the solvent.

The reaction time varies depending upon the reaction temperature. In general, the reaction may be conducted for a time ranging from several minutes to several tens of hours. The end point of the reaction can be determined by monitoring the reaction with a known analysis means (for example, liquid chromatography, thin-layer chromatography, IR or the like).

The sulfur-containing compounds represented by formulas (2-a) to (2-c) can each be isolated by subjecting the reaction product to usual post-treatment operations (for example, neutralization, filtration, extraction in a solvent, washing with water, separation into layers, removal of the solvent by distillation). By known operations and purification methods (for example, distillation, recrystallization, column chromatography, treatment with activated carbon, and the like), their purity can be increased further if necessary.

As specific examples of the sulfur-containing compounds represented by formulas (2-a) to (2-c), the compounds shown below in Table 2 can be exemplified.

TABLE 2

| Illustrative Compound No. | Structural formula |
|---|---|
| 2-1 | 1,3-dithiolane-2-yl-CH$_2$-Br |
| 2-2 | 1,3-dithiolane-2-yl-(CH$_2$)$_2$-Br |
| 2-3 | 1,3-dithiolane-2-yl-(CH$_2$)$_3$-Br |
| 2-4 | 1,3-dithiolane-2-yl-(CH$_2$)$_4$-Br |
| 2-5 | 4-methyl-1,3-dithiolane-2-yl-(CH$_2$)$_2$-Br |
| 2-6 | 4-ethyl-1,3-dithiolane-2-yl-(CH$_2$)$_2$-Br |
| 2-7 | 4-n-butyl-1,3-dithiolane-2-yl-(CH$_2$)$_2$-Br |
| 2-8 | 4,5-dimethyl-1,3-dithiolane-2-yl-(CH$_2$)$_2$-Br |
| 2-9 | hexahydro-1,3-benzodithiol-2-yl-(CH$_2$)$_2$-Br |
| 2-10 | 1,3-dithian-2-yl-CH$_2$-Br |
| 2-11 | 1,3-dithian-2-yl-(CH$_2$)$_2$-Br |
| 2-12 | 1,3-dithian-2-yl-(CH$_2$)$_3$-Br |
| 2-13 | 1,3-dithian-2-yl-(CH$_2$)$_4$-Br |
| 2-14 | 1,3-dithiepan-2-yl-(CH$_2$)$_2$-Br |
| 2-15 | 1,3-dithiolane-2-yl-(CH$_2$)$_2$-Cl |
| 2-16 | 1,3-dithian-2-yl-(CH$_2$)$_2$-Cl |
| 2-17 | 1,3-dithiolane-2-yl-CH$_2$-SH |
| 2-18 | 1,3-dithiolane-2-yl-(CH$_2$)$_2$-SH |

TABLE 2-continued
| Illustrative Compound No. | Structural formula |
|---|---|
| 2-19 | 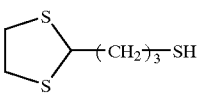 |
| 2-20 | 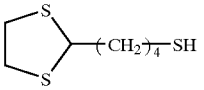 |
| 2-21 | 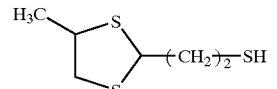 |
| 2-22 | 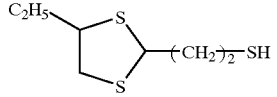 |
| 2-23 | 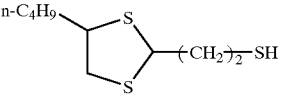 |
| 2-24 | 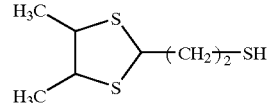 |
| 2-25 | 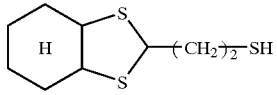 |
| 2-26 | 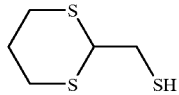 |
| 2-27 | 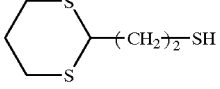 |
| 2-28 | 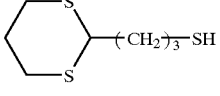 |
| 2-29 | 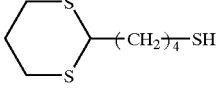 |
| 2-30 | 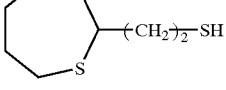 |
| 2-31 | 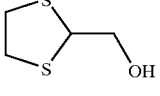 |
TABLE 2-continued
| Illustrative Compound No. | Structural formula |
|---|---|
| 2-32 | 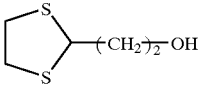 |
| 2-33 | 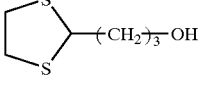 |
| 2-34 | 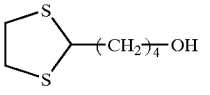 |
| 2-35 | 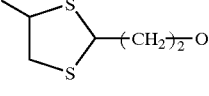 |
| 2-36 | 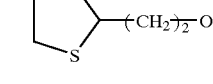 |
| 2-37 | 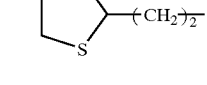 |
| 2-38 | 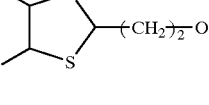 |
| 2-39 | 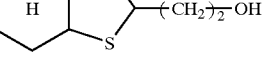 |
| 2-40 | 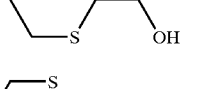 |
| 2-41 |  |
| 2-42 |  |
| 2-43 |  |
| 2-44 | 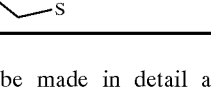 |
A description will next be made in detail about the polymerizable composition which comprises the sulfur-containing (meth)acrylic ester compound represented by formula (1) according to the present invention.

The polymerizable composition according to the present invention contains, as essential components, the sulfur-containing (meth)acrylic ester compound represented by formula (1) according to the present invention and a photo- and/or thermopolymerization initiator. Here, the above-described, sulfur-containing, unsaturated carboxylic ester compounds may be used singly, or a plurality of different sulfur-containing (meth)acrylic ester compounds may be used in combination without developing inconvenience.

In addition to the sulfur-containing (meth)acrylic ester compound represented by formula (1), the polymerizable composition according to the present invention may also contain a known polymerizable compound (photo- or thermopolymerizable monomer, oligomer or the like) to extent not impairing the desired effects as needed without developing inconvenience.

No particular limitation is imposed on the amount of the sulfur-containing (meth)acrylic ester compound represented by formula (1) and contained in the above-described polymerizable composition. In general, however, it may be contained in a proportion of 10 wt. % or more, preferably 20 wt. % or more, more preferably 30 wt. % or more, still more preferably 50 wt. % or more based on the whole polymerizable composition.

No particular limitation is imposed on the polymerization initiator for use in the polymerizable composition according to the present invention. Various known thermopolymerization initiators or photo-polymerization initiators can be used. Illustrative of photopolymerization initiators are benzoin, benzil, benzoin methyl ether, benzoin isopropyl ether, acetophenone, 1,1-dimethoxy-1-phenylacetophenone, 1,1-dichloroacetophenone, 1-hydroxycyclohexylphenyl ketone, 2-hydroxy-2-methyl-1-phenylpropan-1-one, 2-methyl-1-(4-methylthiophenyl)-2-morpholinolpropan-1-one, N,N-dimethylaminoacetophenone, 2-methylanthraquinone, 2-ethylanthraquinone, 2-tert-butylanthraquinone, 1-chloroanthraquinone, 2-amylanthraquinone, 2-isopropylthioxanthone, 2,4-dimethylthioxanthone, 2,4-diethylthioxanthone, 2,4-diisopropylthioxanthone, acetophenone dimethylketal, benzophenone, 4-methylbenzophenone, 4,4'-dicyclobenzophenone, 4,4'-bisdiethylaminobenzophenone, and Michler's ketone. They can be used either singly or in combination.

The photopolymerization initiator may be used in a proportion of from 0.001 to 50 parts by weight, preferably from 0.01 to 30 parts by weight, more preferably from 0.1 to 10 parts by weight, still more preferably from 0.2 to 5 parts by weight per 100 parts by weight of the sulfur-containing (meth)acrylic ester compound represented by formula (1).

Illustrative of the thermopolymerization initiators are peroxides such as benzoyl peroxide, p-chlorobenzoyl peroxide, diisopropyl peroxycarbonate, di-2-ethylhexyl peroxycarbonate and tert-butyl peroxypivalate; and azo compounds such as azobisisobutyronitrile.

The thermopolymerization initiator may be used in a proportion of from 0.001 to 50 parts by weight, preferably from 0.01 to 30 parts by weight, more preferably from 0.1 to 10 parts by weight, still more preferably from 0.2 to 5 parts by weight per 100 parts by weight of the sulfur-containing (meth)acrylic ester compound represented by formula (1).

Examples of the known polymerizable compound as a polymerizable compound usable in the polymerizable composition according to the present invention, said known polymerizable compound being other than the sulfur-containing (meth)acrylic ester compound represented by formula (1), include:

monofunctional or polyfunctional (meth)acrylates such as:
  methyl (meth)acrylate, butyl (meth)acrylate, 2-ethylhexyl (meth)acrylate, ethylcarbitol (meth)acrylate, lauryl (meth)acrylate, tetracyclododecyl (meth)acrylate, phenoxyethyl (meth)acrylate, nonylphenoxyethyl (meth)acrylate, dicyclopentenyl (meth)acrylate, isobornyl (meth)acrylate, N-n-butyl-O-(meth)acryloyloxy-ethyl carbamate, acryloylmorpholine, trifluoroethyl (meth)acrylate, tribromobenzyl (meth)acrylate, and perfluorooctylethyl (meth)acrylate, ethylene glycol di(meth)acrylate, propylene glycol di(meth)acrylate, neopentyl glycol di(meth)acrylate, and 1,6-hexanediol di(meth)acrylate, triethylene glycol di(meth)acrylate, tripropylene glycol di(meth)acrylate, polyethylene glycol di(meth)acrylate, and polypropylene glycol di(meth)acrylate, 2,2-bis(4-acryloyloxyphenyl)propane, 2,2-bis(4-methacryloyloxyphenyl)propane, bis(4-acryloyloxyphenyl)methane, bis(4-methacryloyloxyphenyl)methane, 4,4'-bis(acryloyloxy)-diphenyl sulfide, 4,4'-bis(methacryloyloxy)diphenyl sulfide, 2,2-bis[4-(acryloyloxyethoxy)phenyl]propane, 2,2-bis[4-(methacryloyloxyethoxy)phenyl]propane, 2,2-bis[4-(2-acryloyloxypropoxy)phenyl]propane, 2,2-bis[4-(2-methacryloyloxypropoxy)phenyl]propane, bis[4-(acryloyloxyethoxy)phenyl]methane, bis[4-(methacryloyloxyethoxy)phenyl]methane, bis[4-(2-acryloyloxypropoxy)phenyl]methane, and bis[4-(2-methacryloyloxypropoxy)phenyl]methane, 4,4'-bis(2-acryloyloxyethoxy)diphenyl sulfide, 4,4'-bis(2-methacryloyloxyethoxy)diphenyl sulfide, 4,4'-bis(2-acryloyloxypropoxy)diphenyl sulfide, and 4,4'-bis(2-methacryloyloxypropoxy)diphenyl sulfide, 4,4'-bis(2-acryloyloxyethoxy)diphenylsulfone, 4,4'-bis(2-methacryloyloxyethoxy)diphenylsulfone, 4,4'-bis(2-acryloyloxypropoxy)diphenylsulfone, and 4,4'-bis(2-methacryloyloxypropoxy)diphenylsulfone, 2,2-bis(4-hydroxyphenyl)propane-ethylene oxide or propylene oxide adduct di(meth)acrylate, bis(4-hydroxyphenyl)methane-ethylene oxide or propylene oxide adduct di(meth)acrylate, and 4,4'-dihydroxyphenyl sulfide-ethylene oxide or propylene oxide adduct di(meth)acrylate, trimethylolpropane tri(meth)acrylate, dipentaerythritol pentacrylate, pentaerythritol triacrylate, pentaerythritol tetracrylate, ditrimethylol tetracrylate, dipentaerythritol hexacrylate, 2-(meth)acryloyloxyethyl trisisocyanate, and (meth)acryloyloxypropyl tris(methoxy)silane;

epoxy (meth)acrylates obtained by causing (meth)acrylic acid compounds to act on various known monovalent, divalent or higher valent epoxy compounds, such as:
  phenol glycidyl ether, ethylene glycol diglycidyl ether, propylene glycol diglycidyl ether, resorcin diglycidyl ether, hydroquinone diglycidyl ether, bis(4-hydroxyphenyl)methane (common name: bisphenol F) diglycidyl ether, 2,2-bis(4-hydroxyphenyl)propane (common name: bisphenol A) diglycidyl ether, 4,4'-bishydroxyphenyl sulfide diglycidyl ether, 4,4'-bishydroxyphenylsulfone (common name: bisphenol S) diglycidyl ether, 4,4'-biphenol diglycidyl ether, 3,31,5,5'-tetramethyl-4,4'-biphenol diglycidyl ether, and tris(2,3-epoxypropyl) isocyanurate;

epoxy (meth)acrylates obtained by causing (meth)acrylic acid compounds to act on various known epoxy resins, such as:
  epoxy resins of the phenolic novolak type, epoxy resins of the cresolic novolak type, epoxy resins of the phenol-aralkyl resin type, and epoxy resins of the bisphenol type;
vinyl compounds such as:
  vinylbenzene, divinylbenzene, trivinylbenzene, isopropenylbenzene, diisopropenylbenzene, triisopropenylbenzene, N-vinylpyrrolidone, and N-vinylcaprolactam;
a variety of known polymerizable monomers, for example, allyl-containing compounds such as:
  ethylene glycol diallyl carbonate, triallyl trimellitate, and triallyl isocyanurate; and
a variety of known polymerizable oligomers such as:
  polyurethane (meth)acrylates, epoxy (meth)acrylates, polyester (meth)acrylates, and polyether (meth)acrylates.

To better achieve the effects of the present invention, such a polymerizable compound may be used generally in a proportion of from 300 parts by weight or less, preferably in a proportion of from 200 parts by weight or less, more preferably in a proportion of from 100 parts by weight or less per 100 parts by weight of the sulfur-containing (meth)acrylic ester compound represented by formula(1).

As a specific production process of the polymerizable composition according to the present invention, it can be obtained using the sulfur-containing (meth)acrylic ester compound represented by formula (1) according to the present invention optionally in combination with one or more of the above-described various known polymerizable compounds, adding the above-described polymerization initiator, and then mixing them into a solution. This polymerizable composition is provided for polymerization and curing after filtering off insoluble matter, foreign matter and the like and sufficiently defoaming the filtered composition under reduced pressure as needed.

Upon producing the polymerizable composition, various known additives can be added as desired, including internal mold releasing agents, light stabilizers, ultraviolet absorbents, antioxidants, color pigments (for example, cyanine green, cyanine blue, etc.), dyes, flow modifiers, and inorganic fillers (for example, talc, silica, alumina, barium sulfate, magnesium oxide, etc.).

The cured product and the optical part comprising the cured product according to the present invention are each obtained by polymerizing and curing the above-described polymerizable composition. As their production processes, various processes known to date can be selectively adopted and practiced. Typically, cast polymerization or the like can be mentioned. According to this process, a polymerizable composition obtained as mentioned above is poured into a mold, and is then polymerized using a radical polymerization reaction which is initiated by heat or light.

The mold is composed, for example, of two mirror-polished mold members made of polyethylene, ethylene-vinyl acetate copolymer, polyvinyl chloride or the like and assembled together with a gasket interposed therebetween. Examples of the mold members include the following combinations: glass mold member-glass mold member, glass mold member-plastic plate, and glass mold member-metal plate. As a gasket, the above-described soft thermoplastic resin (polyethylene, ethylene-vinyl acetate copolymer, polyvinyl chloride, or the like) can be used. As an alternative, the two mold members may be fixed together by a polyester adhesive tape or the like. Further, known treatment such as mold releasing treatment may be applied to the mold members.

As mentioned above, examples of the radical polymerization reaction include a polymerization reaction by heat (thermopolymerization), a polymerization reaction by light such as ultraviolet rays (photopolymerization), a polymerization reaction by gamma rays, and processes each making combined use of a plurality of these reactions.

When polymerization is conducted by light, a cast product obtained after parting a mold or an optical part comprising the cured product may be subjected to annealing after completion of curing such that internal stress and strain is eliminated.

Of these processes, photopolymerization by ultraviolet rays permits curing in several seconds to several minutes as opposed to thermopolymerization that requires several hours to several tens of hours, and therefore, is a preferred process from the standpoint of increasing productivity upon production of optical parts according to the present invention.

Upon conducting thermopolymerization, the polymerization temperature varies depending upon the kind of the polymerization initiator and the polymerization conditions, and no limitation is imposed thereon. In general, however, the polymerization temperature ranges from 25 to 200° C., with a range of from 50 to 170° C. being preferred.

As a molding process of an optical lens, the lens can be obtained, for example, by conducting cast polymerization under light and/or heat as mentioned above (for example, JP 60-135901 A, JP 10-67736 A, JP 10-130250 A, etc.).

Described specifically, the molding of an optical lens can be adequately practiced by defoaming a polymerizable composition, which has been prepared by the above-mentioned process and contains a sulfur-containing (meth)acrylic ester compound represented by formula (1) according to the present invention, by a suitable method as needed, pouring it into a mold, and then polymerizing it generally under irradiated light. According to polymerization under heat, on the other hand, the molding of an optical lens can be appropriately practiced by polymerizing such a polymerizable composition while gradually heating it from a low temperature to a high temperature.

The thus-obtained optical lens may be subjected to annealing as needed subsequent to its curing. If necessary, various known physical or chemical treatments can be applied further to prevent reflection, to impart high hardness, to improve abrasion resistance, to impart anti-mist property and/or to impart fashionability, including surface polishing, antistatic treatment, hard coating treatment, non-reflection coating treatment, dyeing treatment, and photochromic treatment (for example, treatment for the provision of a photochromic lens).

As a molding process of a substrate for an optical disk or photomagnetic disk, conventionally known processes can be mentioned including, for example, the process in which a polymerizable composition obtained by the above-described process and containing a sulfur-containing (meth)acrylic ester compound represented by the formula (1) is poured into a cavity of a disk substrate mold, is polymerized by radical polymerization or the like, and if necessary, is subjected to post-heat treatment (JP 58-130450 A, JP 58-137150 A, JP 62-280008 A, etc.), the process in which such a polymerizable composition is subjected to photopolymerization in a mold the upper and lower walls of which are made of glass (JP 60-202557 A), and the process in which, after completion of vacuum casting or pouring of such a polymerizable composition, such a polymerizable composition is pressurized and thermally polymerized (JP 60-203414 A).

The cured product according to the present invention, which is obtained by photopolymerizing the polymerizable composition, and the optical part according to the present invention, which comprises the cured product, are characterized in that they require several minutes to several hours for polymerization and curing, can be polymerized and molded in shorter time than thermosetting optical resins represented by conventional polydiethylene glycol diallyl carbonate and polythiourethane, and have high productivity.

Further, the cured product and optical part according to the present invention have the characteristic features that they are excellent in optical properties, mechanical properties and thermal properties and have high refractive indexes. Specific examples of the optical part include various plastic lenses typified by correctional eyeglass lenses, substrates for optical information recording media, plastic substrates for liquid crystal cells, and coating materials for optical fibers.

The (meth)acrylic ester compounds represented by formula (1) according to the present invention are novel compounds each having the cyclic thioacetal structure in the molecule, and are very useful compounds as raw material monomers of resins for optical members represented by correctional eyeglass lenses.

The present invention will hereinafter be described more specifically based on Examples. It should however be borne in mind that the present invention is not limited to these Examples.

SYNTHESIS EXAMPLE 1

Synthesis of Illustrative Compound No. 2-2 in Table 2; the Compound of Formula (2-c) in Which $R_1$: Hydrogen Atom, $R_2$: Hydrogen Atom, X: Bromine Atom, m: 0, n: 2

Into a glass-made, 500-mL reactor equipped with a stirrer, ethanedithiol (25.4 g, 0.27 mole), a boron trifluoride-ether complex (25 mL) and toluene (100 g) were charged. To the mixture, 2-(2'-bromoethyl)-1,3-dioxolane (53.6 g, 0.275 mole) was added dropwise at 20° C. over 1 hour. After the contents were allowed to react further at 20° C. for 5 hours, iced water (150 g) and toluene (50 g) were added to the reaction mixture, followed by stirring for 15 minutes. The reaction mixture was allowed to stand and separate into phases, so that the reaction product was extracted in the toluene phase. The toluene phase was subjected to alkaline washing with a 3% aqueous solution of sodium hydrogencarbonate (150 g), followed by the washing with water until the water phase became neutral. The toluene phase was separated and taken out. Toluene was distilled off under reduced pressure at 40° C., and the resulting crude product was distilled under reduced pressure to afford 2-(2'-bromoethyl)-1,3-dithiolane (51.8 g) as a colorless liquid.

Yield: 90%, purity>99% [analyzed by gas chromatography (percent by area method)]. Boiling point: 93 to 96° C./0.22 mmHg; $^1$H-NMR δ (CDCl$_3$): 2.2–2.3(m,2H), 3.2(s, 4H), 3.4–3.5(m,2H), 4.6–4.7(t,1H). FD-MS: 212(M), 214 (M+2).

SYNTHESIS EXAMPLE 2

Synthesis of Illustrative Compound No. 2-18 in Table 2; the Compound of Formula (2-a) in Which $R_1$: Hydrogen Atom, $R_2$: Hydrogen Atom, m: 0, n: 2

Into a glass-made, 500-mL reactor equipped with a stirrer, thiourea (32.0 g, 0.42 mole) and ethanol (175 g) were charged. To the mixture, the 2-(2'-bromoethyl)-1,3-dithiolane (44.8 g) prepared in Synthesis Example 1 was added dropwise at 50° C. over 35 minutes. The contents were allowed to react further at 80° C. for 4 hours to yield a thiouronium salt. The reaction mixture was analyzed by high-performance liquid chromatography to confirm that the bromine-containing compound as the raw material had been consumed up. To the reaction mixture, 18% aqueous ammonia (200 g) was added dropwise at 50° C. over 10 minutes, followed by the further reaction at 50° C. for 2 hours to hydrolyze the thiouronium salt. Toluene (100 g) was added, and the resulting mixture was allowed to separate into phases, so that the reaction product was extracted in the toluene phase. The toluene phase was washed with water until the washing became neutral. The toluene phase was then taken out. Toluene was distilled off under reduced pressure at 40° C., and the resulting crude product was distilled under reduced pressure to afford 2-(2'-mercaptoethyl)-1,3-dithiolane (31.6 g) as a colorless liquid.

Yield: 95%, purity>99% [analyzed by gas chromatography (percent by area method)]. Boiling point: 98 to 100° C./0.25 mmHg $^1$H-NMR δ (CDCl$_3$): 1.7–1.8 (br, 1H), 2.0–2.1 (m, 2H), 2.5–2.7 (m, 2H), 3.2–3.3 (m, 4H), 4.7–4.8 (t, 1H). FD-MS: 166(M).

SYNTHESIS EXAMPLE 3

Synthesis of Illustrative Compound No. 2-32 in Table 2; the Compound of Formula (2-b) in Which $R_1$: Hydrogen Atom, $R_2$: Hydrogen Atom, m: 0, n: 2

Into a glass-made, 100-mL reactor equipped with a stirrer, the 2-(2'-bromoethyl)-1,3-dithiolane (21.3 g, 0.10 mole) prepared in Synthesis Example 1, sodium formate (13.6 g, 0.20 mole) and tetramethylammonium bromide (1.61 g, 0.005 mole) were charged. The mixture was stirred for 1.5 hours under heating at 110° C. After completion of a reaction, a 50% aqueous solution of sodium hydroxide (8.8 g) was added under stirring to the reaction mixture over 15 minutes. The reaction product was extracted with toluene. Subsequent to washing of the extract with water, toluene was distilled off under reduced pressure at 40° C., and the resulting crude product was distilled under reduced pressure to afford 2-(2'-hydroxyethyl)-1,3-dithiolane (13.5 g) as a colorless liquid.

Yield: 90%, purity>99% [analyzed by gas chromatography (percent by area method)]. Boiling point: 100 to 105° C./0.25 mmHg $^1$H-NMR δ (CDCl$_3$): 2.0–2.1 (m, 2H), 2.5–2.6 (br, 1H), 2.8–2.9 (m, 2H), 3.2–3.3 (m, 4H), 4.7–4.8 (t, 1H). FD-MS: 150(M).

SYNTHESIS EXAMPLE 4

Synthesis of Illustrative Compound No. 2-5 in Table 2; the Compound of Formula (2-c) in Which $R_1$: Methyl Group, $R_2$: Hydrogen Atom, X: Bromine Atom, m: 0, n: 2

In a similar manner as in Synthesis Example 1 except for use of 1,2-propanedithiol in place of ethanedithiol, synthesis was conducted to afford 2-(2'-bromoethyl)-4-methyl-1,3-dithiolane as a colorless liquid.

FD-MS: 226(M), 228(M+2).

SYNTHESIS EXAMPLE 5

Synthesis of Illustrative Compound No. 2-21 in Table 2; the Compound of Formula (2-a) in Which $R_1$: Methyl Group, $R_2$: Hydrogen Atom, p: 0, q: 2

In a similar manner as in Synthesis Example 2 except for use of the 2-(2'-bromoethyl)-4-methyl-1,3-dithiolane produced in Synthesis Example 4, synthesis was conducted to afford 2-(2'-mercaptoethyl)-4-methyl-1,3-dithiolane as a colorless liquid.

FD-MS: 180(M).

SYNTHESIS EXAMPLE 6

Synthesis of Illustrative Compound No. 2-1 in Table 2; the Compound of Formula (2-c) in Which $R_1$: Hydrogen Atom, $R_2$: Hydrogen Atom, X: Bromine Atom, m: 0, n: 1

In a similar manner as in Synthesis Example 1 except for use of 2-bromomethyl-1,3-dioxolane in place of 2-bromoethyl-1,3-dioxolane, synthesis was conducted to afford 2-bromomethyl-4-methyl-1,3-dithiolane as a colorless liquid.

FD-MS: 198(M), 200(M+2).

SYNTHESIS EXAMPLE 7

Synthesis of Illustrative Compound No. 2-17 in Table 2; the Compound of Formula (2-a) in Which $R_1$: Hydrogen Atom, $R_2$: Hydrogen Atom, m: 0, n: 1

In a similar manner as in Synthesis Example 2 except for use of the 2-bromomethyl-1,3-dithiolane produced in Synthesis Example 6, synthesis was conducted to afford 2-mercaptomethyl-4-methyl-1,3-dithiolane as a colorless liquid.

FD-MS: 152(M).

EXAMPLE 1

Synthesis of Illustrative Compound No. 1-2; the Compound of Formula (1) in Which $R_1$: Hydrogen Atom, $R_2$: Hydrogen Atom, $R_3$: Hydrogen Atom, $X_1$: Sulfur Atom, m: 0, n: 2

Into a glass-made, 500-mL reaction vessel equipped with a stirrer, the 2-(2'-mercaptoethyl)-1,3-dithiolane produced in Synthesis Example 2 (100 g, 0.60 mole) was weighed, to which 3-chloropropionic acid chloride (80 g, 0.63 mole) was added dropwise at 40° C. over 15 minutes. After the contents were reacted further under stirring at 40° C. for 8 hours, toluene (200 g) was added to the reaction mixture to dissolve the same. The resulting solution was transferred into a separating funnel, in which the solution was washed three times with a 3 wt. % aqueous solution of sodium hydrogen carbonate (300 g). After the organic layer (toluene solution) was washed with purified water (300 g) until the water layer became neutral, the organic layer was taken out, and toluene was then distilled off under reduced pressure to afford 2-[2-(3-chloropropionylthio)ethyl]-1,3-dithiolane (127 g).

To a solution of the 2-[2-(3-chloropropionylthio)-ethyl]-1,3-dithiolane (127 g, 0.49 mole) obtained as described above and dissolved in acetone (200 g) in a glass-made 1-L reaction vessel, triethylamine (74 g, 0.73 mole) was added dropwise at 25° C. over 1 hour. After the contents were stirred and reacted at 25° C. for 6 hours, toluene (400 g) and water (400 g) were added to the reaction mixture, and a toluene layer with the reaction product extracted therein was allowed to separate and was taken out. The toluene solution was washed with a 5 wt. % aqueous solution of hydrochloric acid, and the resulting mixture was washed with water until the water layer became neutral. Toluene was then distilled off under reduced pressure to afford the target compound, 2-(2'-acryloylthioethyl)-1,3-dithiolane, (106 g) as a colorless viscous clear liquid. Yield: 80%, purity>99% [analyzed by liquid chromatography (percent by area method)]. $^1$H-NMR δ (CDCl$_3$): 2.0–2.1 (m, 2H), 2.5–2.7 (m, 2H), 3.2–3.3 (m, 4H), 4.7–4.8 (t, 1H), 5.0–7.0 (m, 3H). FD-MS: 220(M).

EXAMPLE 2

Synthesis of Illustrative Compound No. 1-44; the Compound of Formula (1) in Which $R_1$: Hydrogen Atom, $R_2$: Hydrogen Atom, $R_3$: Methyl Group, $X_1$: Oxygen Atom, m: 0, n: 2

To a mixed solution consisting of the 2-(2'-hydroxyethyl)-1,3-dithiolane (30.0 g, 0.20 mole) produced in Synthesis Example 3, pyridine (19.0 g, 0.24 mole) and chloroform (200 g), methacrylic acid chloride (19.9 g, 0.22 mole) was added under ice cooling (at 10° C.). After completion of the dropwise addition, the contents were stirred and reacted further at 10° C. for 3 hours. Byproduced pyridine hydrochloride was then filtered off. After the chloroform solution as the filtrate was washed with dilute hydrochloric acid (200 g), the chloroform solution was washed with water until the washing become neutral. The resulting mixture was allowed to separate into layers, and the organic layer was taken out. Chloroform was distilled off under reduced pressure at 60° C. to obtain the crude reaction product as a pale yellow clear liquid. The crude reaction product was purified by chromatography on silica gel to afford the target product, 2-(2'-methacryloyloxyethyl)-1,3-dithiolane, (34.8 g) as a viscous colorless clear liquid.

Yield: 80%, purity >99% [analyzed by liquid chromatography (percent by area method)].

$^1$H-NMR δ (CDCl$_3$):

1.9–2.0 (s, 2H), 2.1–2.4 (m, 2H), 2.5–2.8 (m, 2H), 3.2–3.3 (m, 4H), 4.7–4.8 (t, 1H), 5.0–7.0 (m, 2H).

FD-MS: 218(M).

EXAMPLE 3

Synthesis of Illustrative Compound No. 1-1; the Compound of Formula (1) in Which $R_1$: Hydrogen Atom, $R_2$: Hydrogen Atom, $R_3$: Hydrogen Atom, $X_1$: Sulfur Atom, m: 0, n: 1

In a similar manner as in Example 1 except for use of the 2-mercaptomethyl-1,3-dithiolane, which had been produced in Synthesis Example 7, as a raw material in place of 2-(2'-mercaptoethyl)-1,3-dithiolane, 2-acryloylthiomethyl-1,3-dithiolane was produced.

FD-MS: 206(M).

Production of Polymerizable Compositions Making use of Sulfur-containing (Meth)acrylic Ester Compounds Represented by Formula (1), and Production of Cured Products by Their Curing Physical properties of cured products or optical parts (lenses) produced in the following Examples and comparative example were determined by the following methods.

External appearance: Tint and transparency were examined visually.

Refractive index, Abbe number: Measured at 20° C. by using a Pulfrich reflectometer.

Impact resistance: Determined by dropping a steel ball from a height of 127 cm onto a central part of each minus lens the center thickness of which was 1.5 mm.

EXAMPLE 4

To the sulfur-containing acrylic ester compound (Illustrative Compound No. 1-2; 30 g) obtained above in Example 1, 2-hydroxy-2-methyl-1-phenylpropan-1-one ("Darocur-1173", product of Ciba-Geigy AG; 30 mg) was added as a photopolymerization initiator. They were thoroughly mixed into a solution. After defoamed under sufficiently reduced pressure, the solution was poured into a mold unit composed of glass mold members and a gasket. Using a metal halide lamp (80 W/cm), ultraviolet rays were irradiated for 60 seconds to effect polymerization. After completion of the polymerization, the polymerization product was allowed to gradually cool down, and the thus-molded, cured product was taken out of the mold unit.

The thus-obtained cured product was colorless and transparent, and no optical strain was observed. Its refractive index was 1.645 (nd), and its Abbe number was 36 (vd).

EXAMPLE 5

Preparation of a polymerizable composition and its polymerization under light (ultraviolet rays) were conducted in a similar manner as in Example 4 except for use of the sulfur-containing (meth)acrylic ester compound, which had been produced as Illustrative Compound No. 1-44 in Example 2, in place of the sulfur-containing (meth)acrylic ester compound as Illustrative Compound No. 1-2.

The thus-obtained cured product was colorless and transparent, and no optical strain was observed. Its refractive index was 1.615 (nd), and its Abbe number was 37 (vd).

EXAMPLE 6

Preparation of a polymerizable composition and its polymerization under light (ultraviolet rays) were conducted in a similar manner as in Example 4 except for use of the sulfur-containing (meth)acrylic ester compound, which had been produced as Illustrative Compound No. 1-1 in Example 3, in place of the sulfur-containing (meth)acrylic ester compound as Illustrative Compound No. 1-2.

The thus-obtained cured product was colorless and transparent, and no optical strain was observed. Its refractive index was 1.660 (nd), and its Abbe number was 35 (vd).

The sulfur-containing (meth)acrylic ester compounds according to the present invention were curable (photopolymerizable) by irradiation of light for short time. Further, the resultant cured products each had a high refractive index and a high Abbe number and was good in heat resistance and impact resistance.

EXAMPLE 7

To a mixture consisting of the sulfur-containing (meth) acrylic ester compound (20 g) obtained as Illustrative Compound No. 1-1 in Example 3 and the epoxy acrylate of bisphenol A diglycidyl ether (5 g), 2-hydroxy-2-methyl-1-phenylpropan-1-one (50 mg; 0.2 wt. % based on the weight of the polymerizable compound) was added. The resulting mixture was thoroughly stirred into a solution. Subsequent to thorough defoaming, the resultant liquid was poured into a mold unit composed of glass mold members and a tape and formed to define the shape of a minus lens. After ultraviolet rays were irradiated for 60 seconds by a metal halide lamp, annealing was conducted at 80° C. for 1 hour. After completion of polymerization, the polymerization product was allowed to cool down to room temperature to obtain a colorless transparent minus lens having a diameter of 30 mm and a center thickness of 1.5 mm.

The lens was colorless and transparent, its refractive index and Abbe number were 1.645 (nd) and 35 (vd), respectively, and its heat resistance and impact resistance were good.

INDUSTRIAL APPLICABILITY

Cured products and optical parts, which can be obtained by polymerizing polymerizable compositions containing sulfur-containing (meth)acrylic ester compounds according to the present invention, respectively, are excellent in optical properties, thermal properties and mechanical properties (impact resistance), have high productivity owing to short-time polymerization and curing moldability, and have high refractive indexes.

The sulfur-containing (meth)acrylic ester compounds according to the present invention are very useful, as monomers for photocurable, polymerizable compositions, in applications such as optical materials and dental materials. Optical parts obtained by curing the polymerizable compositions are excellent in optical properties, thermal properties and mechanical properties, are good in productivity and have high refractive indexes, so that they are useful as various plastic lenses represented by correctional eyeglass lenses, substrates for optical information recording media, plastic substrates for liquid crystal cells, coating materials for optical fibers, and the like.

What is claimed is:

1. A sulfur-containing (meth)acrylic ester compound represented by the following formula (1);

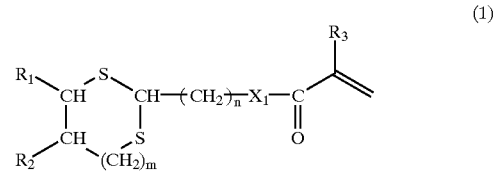

wherein $R_1$ and $R_2$ each independently represent a hydrogen atom or an alkyl group or may be fused together to form a ring, $R_3$ represents a hydrogen atom or a methyl group, $X_1$ represents a sulfur atom, m stands for an integer of from 0 to 3, and n stands for an integer of from 1 to 4.

* * * * *

UNITED STATES PATENT AND TRADEMARK OFFICE
CERTIFICATE OF CORRECTION

| | | |
|---|---|---|
| PATENT NO. | : 6,570,025 B1 | Page 1 of 1 |
| APPLICATION NO. | : 10/048002 | |
| DATED | : May 27, 2003 | |
| INVENTOR(S) | : Kenichi Fujii et al. | |

It is certified that error appears in the above-identified patent and that said Letters Patent is hereby corrected as shown below:

On the title page item (56), under FOREIGN PATENT DOCUMENTS, add:

--EP 1 264 193 09/2001--

Signed and Sealed this

Twentieth Day of February, 2007

JON W. DUDAS
*Director of the United States Patent and Trademark Office*